(12) United States Patent
Brown et al.

(10) Patent No.: US 8,974,736 B2
(45) Date of Patent: Mar. 10, 2015

(54) VOLATILE ARTICLE AND METHOD OF USE

(75) Inventors: Douglas S. Brown, Toledo, OH (US); Jeffrey A. Smith, Perrysburg, OH (US)

(73) Assignee: Fresh Products, Inc., Toledo, OH (US)

( * ) Notice: Subject to any disclaimer, the term of this patent is extended or adjusted under 35 U.S.C. 154(b) by 860 days.

(21) Appl. No.: 12/713,301

(22) Filed: Feb. 26, 2010

(65) Prior Publication Data
US 2011/0114663 A1    May 19, 2011

Related U.S. Application Data

(60) Provisional application No. 61/155,925, filed on Feb. 27, 2009.

(51) Int. Cl.
*A61L 9/12* (2006.01)
*A01M 1/20* (2006.01)

(52) U.S. Cl.
CPC .............. *A61L 9/122* (2013.01); *A01M 1/2033* (2013.01); *A61L 2209/133* (2013.01)
USPC .......................................................... 422/124

(58) Field of Classification Search
CPC ........... A61L 9/012; A61L 9/048; A61L 9/12; A61L 9/122; A61L 9/125
USPC ............... 422/5, 120, 122–124; 215/317–318
See application file for complete search history.

(56) References Cited

U.S. PATENT DOCUMENTS

| | | | |
|---|---|---|---|
| 2,779,624 A | 1/1957 | Friedman | |
| 3,994,439 A | 11/1976 | Van Breen et al. | |
| 4,549,693 A * | 10/1985 | Barlics | 239/58 |
| 4,761,437 A | 8/1988 | Christie | |
| 4,802,626 A | 2/1989 | Forbes et al. | |
| 4,876,070 A | 10/1989 | Tsukahara et al. | |
| 4,915,301 A | 4/1990 | Munteanu | |
| 5,122,401 A | 6/1992 | Finkelstein | |
| 5,259,555 A | 11/1993 | Kiefer | |
| 5,707,696 A | 1/1998 | Boxler | |
| 6,103,201 A | 8/2000 | Green | |
| 7,111,794 B2 | 9/2006 | Timpson | |
| 2003/0044326 A1* | 3/2003 | Yamasaki et al. | 422/124 |
| 2005/0169793 A1* | 8/2005 | Wheatley et al. | 422/124 |
| 2006/0196964 A1* | 9/2006 | Wheatley et al. | 239/57 |

* cited by examiner

*Primary Examiner* — Timothy Cleveland
(74) *Attorney, Agent, or Firm* — Knobbe Martens Olson & Bear LLP

(57) ABSTRACT

A dispenser for a volatile material may be a cover that may be selectively attached to a base to form an internal cavity between them. A method is described for providing a visual indication when an item, such as the cover, needs to be replaced. The cover has a first initial size condition. The volatile material is permitted to evaporate from the cover into the air. The cover is permitted to shrink to a second size condition to provide a visual indication that the cover needs to be replaced.

29 Claims, 3 Drawing Sheets

VOLATILE ARTICLE AND METHOD OF USE

RELATED APPLICATIONS

The present application claims priority to and incorporates by reference in its entirety U.S. provisional patent application Ser. No. 61/155,925 filed on Feb. 27, 2009.

FIELD OF THE INVENTION

The present invention relates to a volatile article and its method of use, including a method of providing a visual indication when the volatile article should be replaced. The invention may be used as a method of providing a visual indication when an air freshening article at least partially constructed of a volatile material should be replaced.

BACKGROUND OF THE INVENTION

Articles for releasing substances, such as sanitizing, deodorizing, freshening, neutralizing or insect repelling substances, into the air are well-known. For example, air freshening articles typically comprise a housing and a separate air freshener composition located within the housing. Typically, the composition is removable from the housing so that upon its exhaustion, it may be removed and replaced.

There are, however, a number of disadvantages associated with the prior art designs. First, by locating the composition within the housing, it may be difficult to know when the composition has been exhausted. Second, labor and material costs are increased by requiring someone to check on the status of the composition which often is not easily discernable and, if it is exhausted, remove it from its housing and replace it with a new composition.

Some prior art designs have electronic monitors that provide an external indication of the status of the composition, but such monitors are expensive, unreliable at times, require maintenance and upkeep themselves and are prone to failure. Further, these electronic monitors serve at the pleasure of the power source to which they are connected. If the power source becomes interrupted or altogether fails or expires, such as with a battery, the ability of the article to release appreciable amounts of the substance, if any at all, may be nil. Failure or malfunction of the monitor is particularly problematic when there is still composition left to be released.

It would therefore be advantageous to provide a simple, inexpensive, reliable and easy to use visual indication when a composition has been exhausted and for that composition to effectively be released into the air. It would also be advantageous for the dispenser to itself be constructed of the volatile material to reduce cost, decrease complexity, and increase ease of use and effectiveness.

SUMMARY OF THE INVENTION

In one embodiment, a cover is provided having an internal surface and an external surface. The cover may be in the shape of a shell-like hemisphere. The cover may be selectively engaged with a base to form a cavity between them. The cover and/or the base may be constructed of a volatile material.

In another embodiment, the present invention is directed toward a method of providing a visual indication when an article, itself made of the volatile material, should be replaced. For example, the cover is in an initial first size condition and it is constructed at least partially of a polymeric plastic infused with a volatile material. The volatile material is permitted to evaporate from the cover into the air. The cover is permitted to shrink to a second size condition to provide a visual indication in physical size that the cover should be replaced.

BRIEF DESCRIPTION OF THE DRAWINGS

The above will become readily apparent to those skilled in the art from the following detailed description when considered in the light of the accompanying drawings in which.

DETAILED DESCRIPTION OF THE PREFERRED EMBODIMENTS

It is to be understood that the invention may assume various alternative orientations and step sequences, except where expressly specified to the contrary. It is also to be understood that the specific devices and processes illustrated in the attached drawings, and described in the following specification are simply exemplary embodiments of the inventive concepts defined in the appended claims. Hence, specific dimensions, directions or other physical characteristics relating to the embodiments disclosed are not to be considered as limiting, unless the claims expressly state otherwise.

Figure 1:
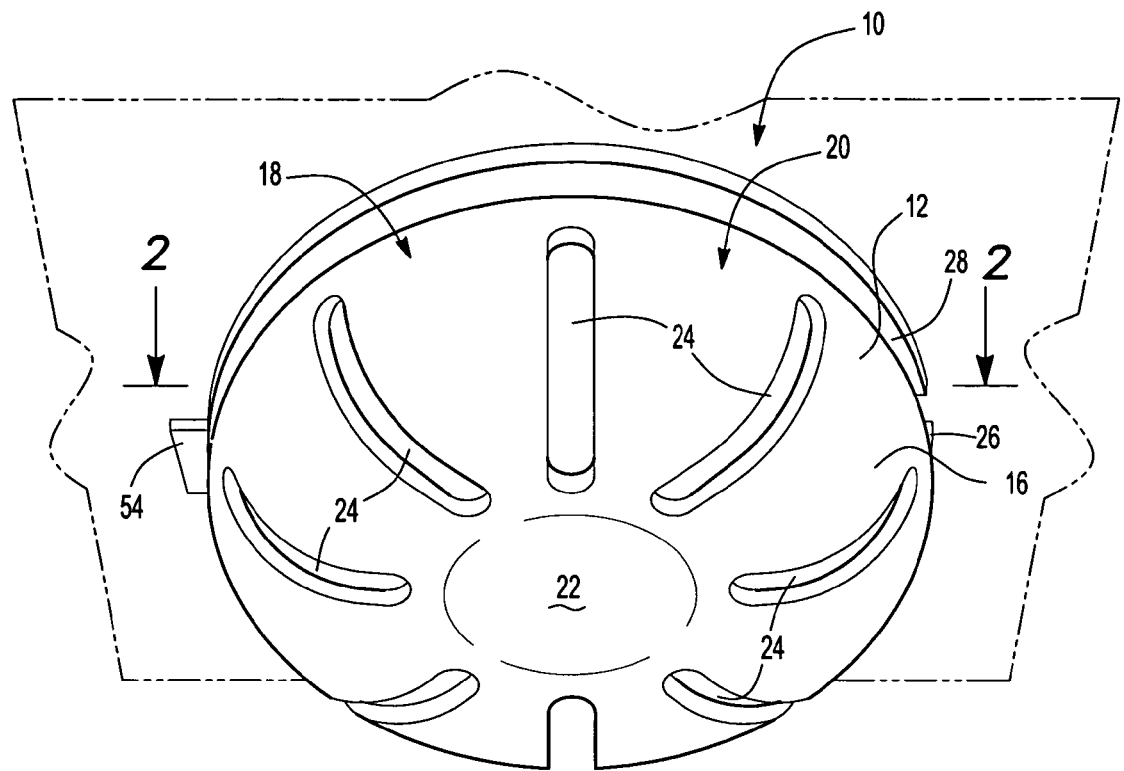
FIG. 1 is a perspective view of one embodiment of the present invention.

Referring now to FIG. 1, one embodiment of the present invention is depicted. The present invention comprises a dispenser 10 for a volatile material where at least part of the dispenser 10 itself is the volatile material. For example, in a preferred embodiment, the present invention depicted in FIG. 1 has a cover 12. The cover 12 has an internal surface 14 and an external surface 16, which may be also seen in FIG. 2. As used herein, the term cover represents the outermost portion of the device that is exposed to view and that conceals, in whole or in part, a base, an airfoil (if any), a motor (if any) and a power source (if any). Preferably, the cover is not blocked from view by any other component of the device.

Figure 2:
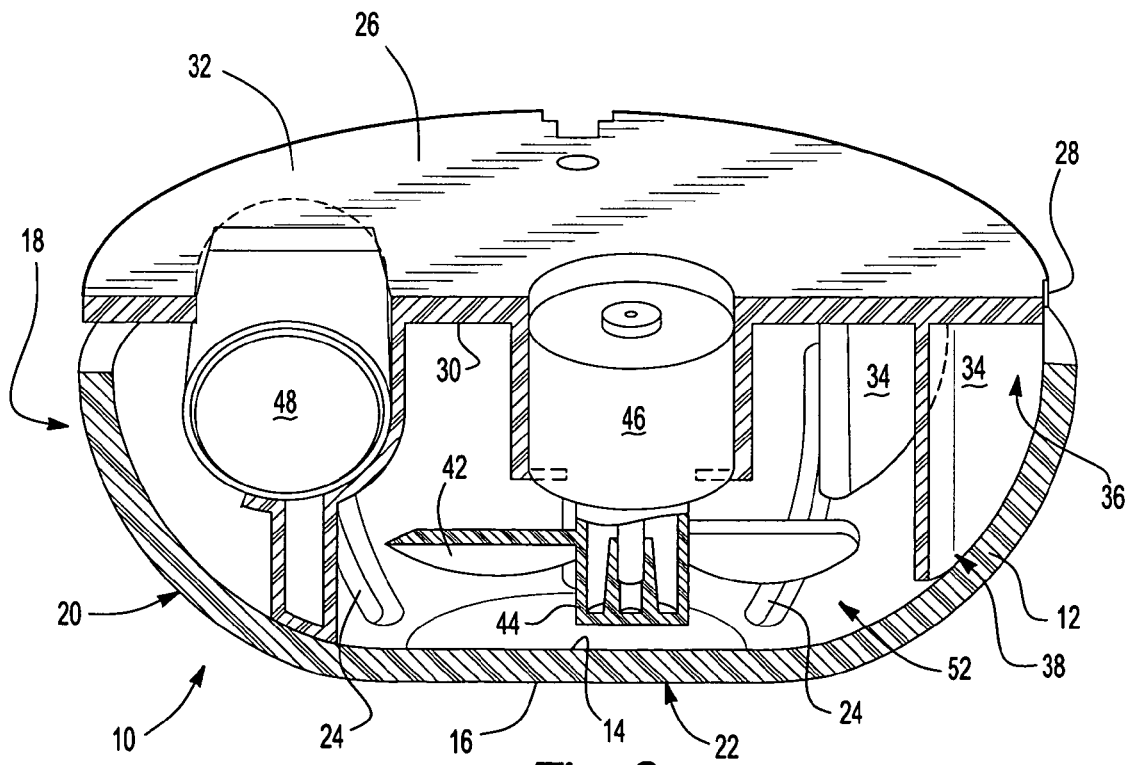
FIG. 2 is a perspective side view along lines 2-2 of FIG. 1 of the present invention.

With continuing reference to FIG. 2, a preferred embodiment depicts the surfaces 14, 16 defining a thickness of material between them that is substantially constant. Those skilled in the art will recognized that various variations in the thickness may be incurred by the method of manufacture utilized but despite these variations the cover 12 still falls within the term substantially constant.

It is also within the scope of the present invention to intentionally vary the thickness of the cover 12 across the entire cover 12 or in selected portions of the cover 12. It will be later appreciated by the following disclosure that this permits for certain areas of the cover 12 to release more or less of the volatile material, thus permitting the cover 12 to be tailored to a particular location or use.

Preferably, the cover 12 is substantially hemispherical is shape, such as the curvilinear hemisphere of a globe. However, in the preferred embodiment, the curved internal surface 14, together with the curved external surface 16, creates the hemisphere into a shell-like structure. A lower perimeter portion 18 of the cover 12 is therefore substantially circular in shape for the depicted embodiment.

The cover 12 is preferably one-piece and integrally formed, although it may be constructed of two or more pieces that may or may not be joined together. Regardless of the number of pieces, the cover 12 may have radiused shoulder portions 20 and a planar or a curvilinear center portion 22.

It is also within the scope of the present invention for the cover 12 to be formed of other shapes. By way of example only, the cover 12 may be in the shape of a rectangle, square, triangle or any polygon. These shapes may have perimeter portions that are the same as the overall shape of the cover 12 or the lower perimeter portions 18 may differ from the overall shape.

FIG. 1 depicts a plurality of apertures 24 in the cover 12. While a plurality of apertures 24 is depicted, the number of apertures 24 may vary from one to any number. Additionally, no aperture may be provided in the cover 12 at all.

The apertures 24 depicted in FIG. 1 are substantially equidistant from one another about the cover 12, although any spacing may be used. In the depicted embodiment, the apertures 24 extend from the circular center portion 22 of the cover 12 radially outward. The apertures 24 are formed in the shape of elongated slots. The apertures 24 are not limited to the depicted design and may instead comprise any shape. Further, each aperture may have a different shape. Additionally, the shape of the center portion 22 may be any design and it is not limited to a circle.

From the foregoing, it can be appreciated that the cover 12 may be provided with a decorative design that is ascetically pleasing. The decorative design may be a result of the overall shape of the cover 12, the design of the apertures 24, or other features.

Figure 3:
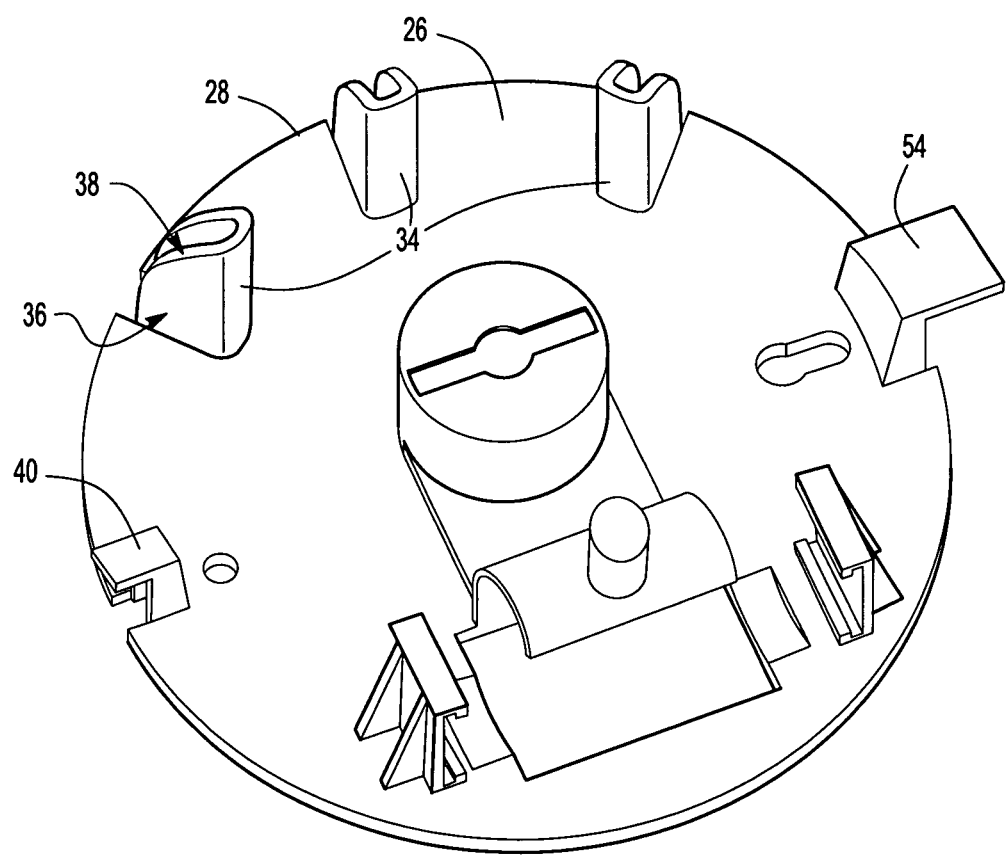
FIG. 3 is a perspective view of a base of the present invention.

In FIG. 2, the cover 12 of FIG. 1 is depicted with a base 26. FIG. 3 depicts the base 26 by itself. Preferably, the base 26 has a complimentary shape to the lower perimeter portion 18 of the cover 12, but this is not required. In the depicted invention, the base 26 has a substantially circular perimeter 28. As used herein, the term substantially circular perimeter includes a perimeter that is entirely circular as well as a perimeter that includes various notches and/or irregularities to accommodate and/or form features of the base 26.

The base 26 has a first surface 30 and a second surface 32. The first surface 30 faces the internal surface 14 of the cover 12. The second surface 32 of the base 26 is opposite the first surface 30. The second surface 32 may be substantially planar. A substantially planar surface assists the base 26 in being connected to a wall or other complimentary planar surface (not shown), whether vertically oriented or horizontally oriented. While a planar second surface 32 is depicted, it may be readily appreciated that the second surface 32 can be formed to be adapted to any surface of any shape or size.

It is preferred that the base 26 is one-piece and integrally formed, however, the base 26 may be 2 or more pieces that may or may not be joined.

The base 26 preferably has a number of upstanding legs 34 that are integrally formed with the base 26. The legs 34 may be of any number including one. An alternative embodiment that is not shown does not require any legs.

The legs 34 in the depicted embodiment have a C-shaped cross-section, although other shapes are permissible. The C-shaped cross-section extends from a C-shaped notch formed in the base 26 itself. The legs 34 may be equally spaced from one another along the base perimeter 28, but the spacing may vary.

A first portion 36 of each leg 34 extends upwardly from the base 26. The first portion 36 transitions to a second portion 38 located above the first portion 36. Preferably, each second portion 38 has a taper, but the first portion 36 may be tapered too. The taper of the second portion 36 preferably follows, and may even contact, the internal surface 14 of the cover 12. The first portion 36 and the second portion 38 of the leg 34 are substantially perpendicular to the first surface 30 of the base 26.

The legs 34 and/or the perimeter 28 of the base 26 may selectively engage the internal surface 14 of the cover 12 to support the cover 12 and may also provide a frictional engagement that selectively secures the two together. Additional, or alternative means, to secure the cover 12 to the base 26, as described below, may be used.

As shown on FIG. 3, a biasing member 40 may be located on the base 26. In the preferred embodiment, the biasing member 40 is integrally formed with the base 26. The biasing member 40 may be such as a hook-like member designed to engage with a continuous or partial rim, or aperture, (not shown) on the internal surface 14 of the cover 12. The biasing member 40 may be located at or near the perimeter 28 of the base 26. The biasing member 40 may be dimensioned such that it is flexible enough to be selectively pushed away from the base perimeter 28 so that it disengages the rim, ledge or aperture to permit the cover 12 to be unlocked from the base 26. Preferably, the biasing member 40 is resilient enough that it moves back into position to engage the cover 12 after being moved away from it.

Turning now to FIG. 2, a rotating airfoil 42 is depicted on the base 26. The airfoil 42 may be such as a fan. The fan may have any number of blades with any number of designs. In one embodiment, the fan has 7 blades. The blades are connected to a hub 44 of the fan. The hub 44 is rotationally mounted substantially in the middle of the base 26, although it may be located anywhere on the base 26. The airfoil 42 may be used with or without the cover 12.

The hub 44 may be connected to an electric motor 46 either directly as shown in FIG. 2, or through gearing, drive belts or the like. The electric motor 46 is provided with a source of energy. The energy source may be such as a battery 48, or a solar cell. Alternatively, the hub 44 may be permitted to rotate freely without any drive mechanism by virtue of air moving within the cover 12.

Another embodiment of the present invention does not have any airfoil. In that embodiment, the invention comprises the cover 12 and the base 26.

A switch (not shown) may be located between the energy source 48 and the motor 46. The switch may be such as an on-off switch, a photocell, or motion sensor or a timer. The cover 12 may function in a protective way for any or all of the features discussed above.

The base 26, the cover 12 and/or the airfoil 42 are preferably constructed, in whole or in part, of a polymeric plastic that has been infused with a volatile material. In a preferred embodiment, the plastic may be such as ethylene vinyl acetate (EVA) by itself or the EVA may be combined with a copolymer. The copolymer may be such as polypropylene, polyethylene, or polyvinyl chloride. The volatile material may comprise 30-65% of the plastic weight. The volatile material may be, but is not limited to, a sanitizing material, a deodorizing material, a freshening material, a neutralizing material and/or a pest repelling material. Examples, which the present invention is not limited to, of pest repelling materials are clove or thyme oil. Examples, also which the present invention is not limited to, of freshening materials are mint, honeysuckle, apple and the like.

In addition, or alternatively, to the volatile material, the base 26, the cover 12 and/or the airfoil 44 may be constructed, in whole or in part, of at least one color changing material. By way of example, approximately 1% leuco crystal violet pigment may be added to any of these structures. Over a predetermined period of time the pigment oxidizes resulting in a color change from white to purple in color. Different pigments may be used for the cover 12, the base 26 and/or airfoil 42 that change colors at different times, or all at the same time.

It is also within the scope of the present invention to construct the base 26, the cover 12 and/or the airfoil 44 of paper, natural or man-made sponge, foam and/or fabric or textile material. In fact, any material capable of absorbing the volatile material and/or pigment may be used.

The present invention also comprises a method of providing a visual indication when the volatile material needs to be replaced. The following steps will be described in the embodiment where the cover 12 is comprised of the volatile material. However, as previously mentioned, the base 26 and/or the airfoil 42 may also be constructed of the same volatile material, or they may be constructed of a different volatile material, or no volatile material may be used for them at all.

The cover 12 is provided in a first initial size condition 50. The cover 12 may be removed from its packaging or the like, if any is provided, and located on the base 26. The cover 12, when located on the base 26, defines a cavity 52. More particularly, the cavity 52 is created between the internal surface 14 of the cover 12 and the first surface 30 of the base 26. The cover 12 and base 26 combination may be located, for example, in a restroom.

The base 26 may be mounted to a wall in the restroom, such as by locating a mechanical fastener through a hanger portion 54 connected to the base 26. The cover 12 is exposed to the air in the room where it is located. The volatile material, or materials, immediately begin to evaporate, or otherwise disperse into minute particles, from the cover 12 into the surrounding air. The surrounding air thus becomes sanitized, deodorized, freshened, and/or malodors are neutralized and/or the pest repelling material disperses into the air. Alternatively, or additionally, the color changing material may begin its oxidation process, or other chemically related change depending on the material used.

Due to the fact that the volatile material comprises a significant portion of the cover 12, its evaporation from the cover 12 causes the cover 12 to change in size over time to an extent that the change is visually perceptible. The cover 12 thus changes in size from its first initial size condition 50 to a second size condition 56 that is smaller than the first size condition 50.

Figure 4:
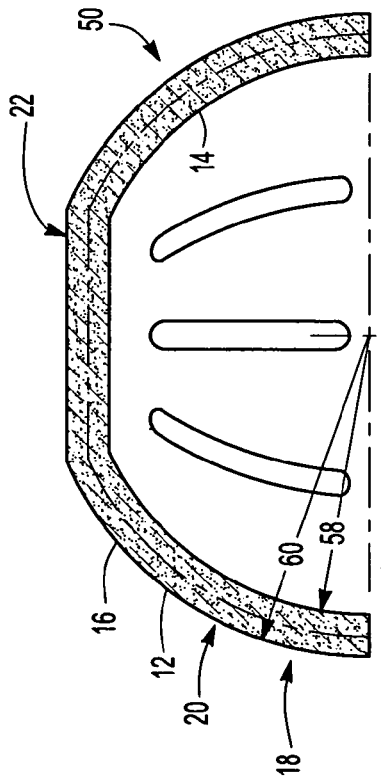
FIG. 4 is sectional view of a cover of the present invention in a first condition.
Figure 5:
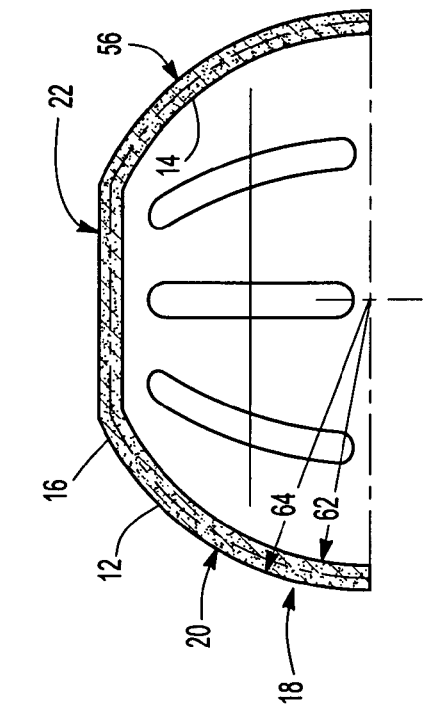
FIG. 5 is a sectional view of the cover in FIG. 4 in a second condition.

FIGS. 4 and 5 provide one example of the change in size of the cover 12 from the first size condition 50 to the second, smaller size condition 56. In FIG. 4, the internal surface 14 has a radius 58 and the external surface 16 has a radius 60. FIG. 5 depicts the same cover 12 after the volatile material has significantly evaporated from the cover 12. Here, the internal surface 14 has a radius of 62, where 62 is less than 58, and an external surface radius of 64, where 64 is less than 60.

The cover 12 may shrink by approximately 10-30% of its original size as a result of the evaporation of the volatile material. One embodiment of the cover 12 shrinks to approximately 20% of the first size condition 50 when a majority of the volatile material has evaporated. In this case, a majority means approximately 75-95% of the volatile material. Thus, by way of example only, where one embodiment of the cover 12 has an outer diameter of approximately 4.5 inches when it is initially installed, the outer diameter of the cover 12 may shrink to approximately 3.6 inches once a majority of the volatile material has evaporated.

The amount of evaporation of the volatile material is a function of many factors including, but not limited to, temperature, humidity, the degree of air circulation about the cover 12, the thickness of the cover 12, the amount of volatile material in the cover 12 and/or the kind of copolymer, if any, included with the EVA.

The significant change in the dimension of the cover 12 is readily perceptible. The change in the cover 12 from the first size condition 50 to the second size condition 56 makes it easy for a person to understand that the sanitizing, deodorizing, freshening, and/or malodors neutralizing and/or the pest repelling ability of the cover 12 has been significantly reduced from the condition of the cover 12 when it was initially installed. The person can therefore easily remove the depleted cover from the base 26 and replace it with a new cover 12.

Despite this noticeable change in the size of the cover 12, it may be readily removed from the base 26. The cover 12 is designed so that in its first size condition 50, it fits somewhat loosely on the base 26. As the volatile material evaporates, the cover 12 shrinks and fits more tightly on the base 26. It is preferred that the cover 12 does not shrink to the point that it comes off of the base 26 by itself.

As previously mentioned, the thickness of the cover 12 may vary. By way of example only, it may be possible to reduce the thickness of the cover from 0.180" to approximately 0.100" in selected areas. It has been found that the volatile material evaporates faster in areas where the cover thickness has been reduced. The size change in these areas thus becomes particularly noticeable. It may therefore be appreciated that prominent areas of the cover 12, such as the center portion 22, may be reduced in thickness so that their size change is more noticeable as compared to the size change in other areas of the cover 12.

Figure 6:
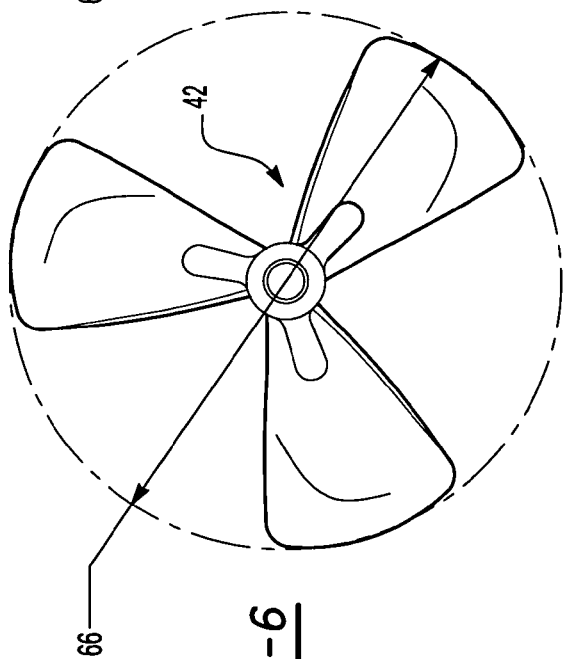
FIG. 6 is a plan view of one embodiment of an airfoil of the present invention in a first condition.
Figure 7:
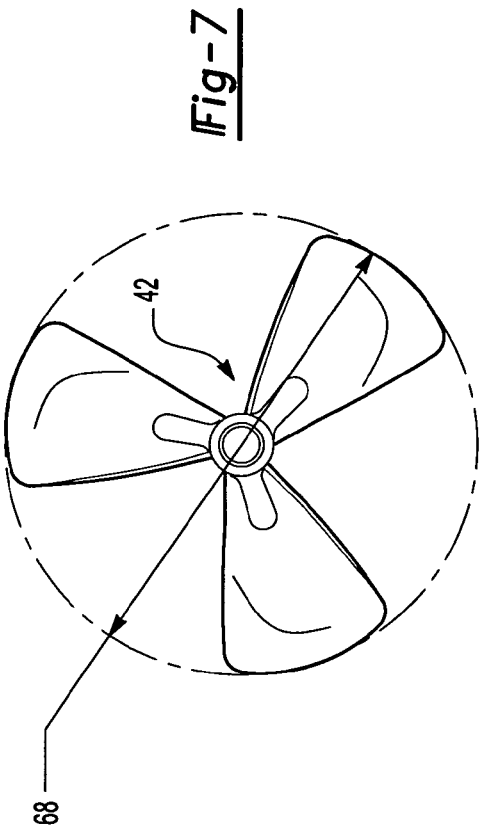
FIG. 7 is a plan view of the airfoil in FIG. 6 is a second condition.

FIGS. 6 and 7 depict a similar shrinkage of an airfoil 42 that has been constructed of the volatile material in similar proportions to that of the cover 12. FIG. 6 depicts the airfoil 42 having a predetermined diameter 66 in a first initial, or unused, condition. FIG. 7 depicts the same airfoil 42 having a reduced diameter 68 as a result of exposure to air and permitting the volatile material to significantly evaporate from the airfoil 42. The diameter 68 is significantly less than diameter 66 permitting a clear visual indication to a person that the volatile material is no longer present in an effective quantity in the airfoil 42. The installed airfoil 42 may then be readily replaced with a new airfoil 42 that is fully loaded with the volatile material. Changes in size of the airfoil 42 are similar to those discussed above for the cover 12. Thus, the change in size of the airfoil 42 needs to be changed.

In accordance with the provisions of the patent statutes, the present invention has been described in what is considered to represent its preferred embodiments. However, it should be noted that the invention can be practiced otherwise than as specifically illustrated and described without departing from its spirit or scope.

What is claimed is:

1. A dispenser comprising:
    a hemispherical shell-like cover having an internal surface and at least one aperture extending through said cover, the internal surface of said hemispherical shell-like cover having a generally hemispherical shape and having an outer perimeter portion;
    a base that said cover is selectively attached to, said base having a first surface and a second surface, wherein said first surface and said cover define a cavity of said dispenser, and said outer perimeter portion of said cover and said first surface cooperate to define at least one inlet opening, said second surface configured to be mounted against a wall; and a fan mounted on said base and positioned within said cavity, said fan including plurality of blades which are spaced farther from said first surface of the base than said perimeter of said cover is spaced from said first surface when said cover is attached to said base, so that air is drawn by said plurality of blades through said at least one inlet opening, is forced along said internal surface of said cover and is forced through said at least one aperture in the cover and said cover substantially surrounding said plurality of blades of said fan;

a mount connected to said base to an energy source for said fan;

wherein said cover is a combined material comprising a polymeric plastic comprising ethylene vinyl acetate infused with a scent, so that air is drawn by said plurality of blades through said at least one inlet opening, is forced along said internal surface of said cover and through said at least one aperture to project the scent into the area surrounding said dispenser.

2. The dispenser of claim 1, wherein at least two legs are integrally formed with said base, said legs extend into said cavity and contact the internal surface of said cover.

3. The dispenser of claim 1, wherein said second surface of said base is substantially planar and bounded by a substantially circular perimeter.

4. The dispenser of claim 1, wherein a motor is located within said cavity and is supported on said base.

5. The dispenser of claim 1, wherein said fan is a polymeric plastic infused with a volatile material.

6. The dispenser of claim 1, wherein a biasing member is integrally formed with a perimeter portion of said base, said biasing member selectively securing said cover to said base.

7. The dispenser of claim 1, wherein said scent is infused entirely throughout said cover.

8. The dispenser of claim 1, wherein said scent is infused in selective portions of said cover.

9. The dispenser of claim 1, wherein said cover is infused with at least a second scent.

10. The dispenser of claim 1, wherein said cover comprises a plurality of apertures for ingress and egress of air.

11. The dispenser of claim 1, wherein said base is constructed at least partially of a polymeric plastic infused with a scent.

12. The dispenser of claim 2, wherein said legs have curvilinear upper surfaces that frictionally engage with said internal surface of said cover.

13. The dispenser of claim 1, wherein the dispenser provides visual indication when said scent needs to be replaced due to the release of the scent, wherein the combined material comprises between approximately 30-65% of the scent; and said cover configured to at least partially cover said base;
said combined material being in a first size condition upon attachment to said base; and
said combined material being in a second size condition smaller than said first size condition, which occurs after evaporation of the scent;
wherein said second size condition indicates that said cover should be removed from said base and replaced with a replacement cover.

14. The dispenser of claim 13, wherein said second size condition is approximately 80% smaller than said first size condition.

15. The dispenser of claim 13, wherein the combined material is further combined with a first color, said first color configured to change into a second color when a majority of said scent has evaporated.

16. The dispenser of claim 15, wherein the cover is configured to be removed from said base when said cover changes to said second color, and wherein said cover is further configured to be replaced with another cover after removal.

17. The dispenser of claim 15, wherein said first color is throughout said combined material.

18. The dispenser of claim 15, wherein said first color is in selective portions of said combined material.

19. The dispenser of claim 15, wherein said second color appears throughout said combined material.

20. The dispenser of claim 15, wherein said second color appears in selective portions of said combined material.

21. A dispenser comprising:
a hemispherical shell-like cover having an internal surface and at least one aperture extending through said cover, the internal surface of said hemispherical shell-like cover having an outer perimeter portion;
a base that said cover is selectively attached to, said base having a first surface and a second surface, wherein said first surface and said cover define a cavity of said dispenser, and said outer perimeter portion of said cover and said first surface cooperate to define at least one inlet opening, said second surface configured to be mounted to a flat surface;
a fan mounted on said base and positioned within said cavity, said fan including a plurality of blades which are spaced farther from said first surface of the base than said perimeter of said cover is spaced from said first surface when said cover is attached to said base, so that air is drawn by said plurality of blades through said at least one inlet opening, is forced along said internal surface of said cover and is forced through said at least one aperture in the cover and said cover substantially surrounding said plurality of blades of said fan; and
a mount connected to said base to hold an energy source for said fan;
wherein said cover is a polymeric plastic comprising ethylene vinyl acetate infused with a scent, so that air is drawn by said plurality of blades through said at least one inlet opening, is forced along said internal surface of said cover and through said at least one aperture to project the scent into the area surrounding said dispenser, said base comprising at least a first portion which engages a first portion of said cover, said first portion of said base and said first portion of said cover being manually disengagable from one another to permit said cover and said base to be manually disengaged from one another.

22. The dispenser of claim 21, wherein said first portion of said base comprises a biasing member.

23. The dispenser of claim 22, wherein said first portion comprises a hook-like member.

24. The dispenser of claim 21, wherein a motor is located within said cavity and is supported on said base.

25. The dispenser of claim 21, wherein said scent is infused entirely throughout said cover.

26. The dispenser of claim 21, wherein said cover is infused with at least a second scent.

27. The dispenser of claim 21, wherein said fan is a polymeric plastic infused with a volatile material.

28. The dispenser of claim 21, wherein said cover comprises a plurality of apertures for egress of air.

29. The dispenser of claim 21, wherein the cover is further combined with a first color, said first color configured to change into a second color when a majority of said scent has evaporated.

* * * * *